United States Patent [19]

Molina

[11] 4,011,174
[45] Mar. 8, 1977

[54] WATER WASHABLE DYE PENETRANT COMPOSITION AND METHOD OF APPLICATION

[75] Inventor: Orlando G. Molina, Westminster, Calif.

[73] Assignee: Rockwell International Corporation, El Segundo, Calif.

[22] Filed: May 23, 1975

[21] Appl. No.: 580,258

Related U.S. Application Data

[63] Continuation-in-part of Ser. No. 444,433, Feb. 21, 1974, Pat. No. 3,915,886, and a continuation-in-part of Ser. No. 521,730, Nov. 7, 1974, Pat. No. 3,939,092.

[52] U.S. Cl. ............................ 252/301.19; 73/104; 250/459
[51] Int. Cl.$^2$ ................ C09K 11/06; G01N 19/08; G01N 21/16
[58] Field of Search ............... 252/301.2 P, 301.19; 73/104; 250/459

[56] References Cited

UNITED STATES PATENTS

| | | | |
|---|---|---|---|
| 3,748,469 | 7/1973 | Molina | 250/459 |
| 3,814,695 | 6/1974 | Molina | 252/301.2 P |
| 3,896,664 | 7/1975 | Alburger | 73/104 |
| 3,915,886 | 10/1975 | Molina | 252/301.2 P |

*Primary Examiner*—F.C. Edmundson
*Attorney, Agent, or Firm*—C. T. Silberberg; L. Lee Humphries

[57] ABSTRACT

Water washable substantially biodegradable dye penetrant composition for use in non-destructive dye penetrant inspection of parts for locating cracks and flaws therein, consisting essentially of an organic dye, preferably a fluorescent dye, a carrier or solvent for said dye in the form of certain ethoxylated linear alcohols, particularly the biodegradable nonionic surfactants comprised of ethoxylates of a mixture of secondary alcohols having linear alkyl chains of from 11 to 15 carbon atoms, and an average of from 3 to 12 moles of ethylene oxide, and glycol monobutyl ether for thinning the dye penetrant solution substantially without affecting the sensitivity of the penetrant or its biodegradability, and facilitating application of the liquid dye penetrant composition by spraying to the surface of an object or part to be inspected. In the method of application of the dye penetrant composition, such composition is applied to the surface of an object containing cracks and flaws, water is applied to the surface of the object, preferentially removing the glycol monobutyl ether vehicle or carrier, and almost immediately thereafter removing the remaining dye penetrant distributed on the surface, both the removal of the glycol ether component and the remaining dye penetrant occuring in the same washing operation. The part is then inspected under appropriate lighting conditions such as fluorescent or black light, to obtain colored traces from the dye penetrant remaining in the cracks and flaws.

16 Claims, No Drawings

WATER WASHABLE DYE PENETRANT COMPOSITION AND METHOD OF APPLICATION

This application is a continuation-in-part of my copending applications Ser. No. 444,433, filed Feb. 21, 1974, now Pat. No. 3,915,886 and Ser. No. 521,730, filed Nov. 7, 1974, now Pat. No. 3,939,092.

BACKGROUND OF THE INVENTION

This invention relates to an improved biodegradable dye penetrant composition and method for non-destructively testing material specimens to locate and identify surface voids, cracks or defects, and is particularly concerned with the provision of an improved water washable biodegradable dye penetrant composition or solution containing a specific relatively non-volatile solvent for thinning such water washable dye penetrant, such solvent being preferentially removable from the part surface followed by removal of excess dye penetrant, upon application of water to an object to which the dye penetrant composition has been applied, the dye penetrant composition remaining in the cracks and voids of the part having substantially the same properties as the initial composition in the absence of such solvent, particularly substantially the same sensitivity, the biodegradability of the excess dye penetrant removed from the object surface being substantially unaffected by such solvent. The invention is also concerned with the method of employing such thinned water washable dye penetrant composition in a penetrant inspection process.

In known penetrant inspection methods for rapid location and evaluation of surface flaws or cracks in test bodies or parts, a dye penetrant composition, preferably containing a fluorescent dye, and which will penetrate the openings of the surface cracks or flaws in the part, is applied to the surface of the test body, and the excess penetrant composition is removed from the surface of the body. A developer composition may then be applied to the part surface, which acts as a wick and causes the liquid penetrant containing the fluorescent dye, which was retained in the cracks or surface flaws, to be drawn up out of the surface defects by capillary action. The part is then exposed to appropriate lighting conditions, such as invisible fluorescigenous light, and the location of the surface flaws is revealed by the emission of visible fluorescent light by the penetrant dye which was retained in the cracks or flaws after the penetrant composition was removed from the surface of the part.

For best efficiency, particularly for the detection and location of minute surface cracks and flaws, as well as intermediate size and gross cracks, it is necessary that the dye penetrant composition have high sensitivity.

Volatile type solvents are commonly employed for extending or thinning dye penetrant inspection solutions or compositions. This is done chiefly for the purpose of lowering the viscosity of the penetrant in order to adapt it for application in spraying systems. Thus for example solvents such as kerosene, light fuel oils, and methyl ethyl ketone, all highly volatile solvents, have heretofore been employed in prior art dye penetrants. See for example U.S. Pat. No. 2,806,959.

Another reason for thinning a penetrant solution is the resulting economy due to the extending effect which the solvent has in the penetrant solution. However, for this purpose, the solvent must evaporate quickly after its application to a part surface, otherwise the properties of the penetrant, such as fluorescence and sensitivity are greatly reduced by the presence of a solvent which does not evaporate. Therefore, the use of volatile solvents has heretofore generally been considered necessary for this purpose.

However, the use of volatile solvents in dye penetrant compositions has certain disadvantages. Thus, the use of volatile solvents in dye penetrants results in the evolution of fumes and solvent vapors which are rapidly formed by the evaporating solvent.

An additional criterion has recently developed also with respect to dye penetrant solutions and compositions. Generally, dye penetrant solutions presently being used and containing solvents and wetting agents present a disposal problem in that they are substantially non-biodegradable, that is, they are very difficult to decompose by bacteria in sewage disposal plants. Hence the necessity for the development of dye penetrant solutions and compositions which are biodegradable, that is which employ dye solvents and carriers which are biodegradable, and are readily available despite the petrochemical shortage, has attained considerable importance.

In my above copending applications there is disclosed a novel dye penetrant which has improved washability and sensitivity characteristics, and which is biodegradable, containing as the vehicle for the dye, certain biodegradable nonionic ethoxylated alcohols, or combinations thereof.

In my U.S. Pat. No. 3,777,157 there is disclosed a water washable dye penetrant composition which comprises N-methyl-2-pyrrolidone, a mixture of a ketone and wetting agents, a fluorescent dye and glycol monobutyl ether which functions as a thinner for the dye penetrant composition. Although such dye penetrant composition has been found effective, it has the disadvantages of requiring a multiplicity of dye carriers or solvents, with proper balance thereof necessary to provide a desired sensitivity, and the composition is not biodegradable.

Accordingly, the main object of the present invention is the provision of a water washable biodegradable dye penetrant solution or composition which avoids the use of volatile solvents and its above noted disadvantages, yet which can be readily applied as by spraying to a part surface and readily removed following application of the dye penetrant to a test body, substantially without affecting the properties of the dye penetrant composition, and particularly its sensitivity and biodegradability. An additional object is the provision of procedure for utilizing such improved water washable dye penetrant composition in a dye penetrant inspection method.

DESCRIPTION OF THE INVENTION

It has been found that the above objects and advantages can be accomplished according to the invention, and an improved water washable dye penetrant composition afforded, having good sensitivity for detection of cracks and defects in part surfaces, and which is biodegradable, by employing as a solvent or carrier for the dye, e.g. fluorescent dye, certain biodegradable nonionic surfactants comprised of certain ethoxylated linear alcohols, of the type disclosed in my above copending applications, separately or in admixture, and incorporating the relatively non-volatile solvent, glycol monobutyl ether (otherwise known as ethylene glycol monobutyl ether or 2-butoxy ethanol) and commonly known as butyl Cellosolve. Such glycol monobutyl ether solvent functions as a temporary additional carrier or extender for the dye penetrant, and has the important property and advantage of diluting or thinning a water washable penetrant composition of the type noted above, particularly one containing a fluorescent dye, substantially without affecting or changing the sensitivity of the dye penetrant in the cracks and flaws, following removal of such extender, and substantially without affecting the biodegradability of the excess dye penetrant composition removed from the part surface, following the preferential removal of the glycol monobutyl ether component.

It has been found unexpectedly that the biodegradable dye penetrant composition hereof containing the biodegradable ethoxylated alcohol surfactant essentially as sole carrier for the dye, in contrast to the dye penetrant composition of my above patent containing the entirely different pyrrolidone as carrier and ketone and wetting agents, can be successfully thinned or extended with as much as 150% by volume, of glycol monobutyl ether without affecting the sensitivity of the remaining dye penetrant composition following removal of the glycol monobutyl ether, or the biodegradability of the excess dye penetrant washed from the part surface.

It was also found unexpected that the use of glycol monobutyl ether solvent as an extender in the dye penetrant composition of the invention containing the highly water miscible ethoxylated alcohol surfactants described herein, enhances the washability of the excess dye penetrant composition from a part surface without removing or dislodging the entrapped dye penetrant composition from the surface defects and cracks in the part.

Thus, for detecting cracks and flaws on the surface of a part employing the dye penetrant composition of the invention containing the glycol monobutyl ether solvent, such dye penetrant solution is applied to the surface of the part, and a water wash is applied to the dye penetrant covering the surface, preferentially first removing the glycol monobutyl ether from the dye penetrant, and followed substantially simultaneously by removing or washing away of the remaining liquid dye penetrant containing the dye and ethoxylated alcohol surfactant vehicle, distributed on the surface. However, this is an essentially single step water washing operation, and the preferential removal of such glycol monobutyl ether together with subsequent immediate removal of remaining liquid dye penetrant, both occur in a single washing operation.

The glycol monobutyl ether component is not photochemically reactive and is relatively safe to the environment. Therefore, when washed preferentially from the surface of the object, followed by washing of the remaining or excess dye penetrant containing biodegradable nonionic ethoxylated alcohol surfactant, the biodegradability of such penetrant afforded by the biodegradable nonionic surfactant is not adversely affected by the initial presence therein of glycol monobutyl ether or the presence therein of glycol monobutyl ether following the washing operation.

Further, as previously noted, in view of the marked difference in chemical composition of the solvent carrier in the form of the ethoxylated alcohol surfactant employed in the dye penetrant composition hereof as compared to the pyrrolidone-type carrier containing ketone and additional wetting agents employed in the above patent, it was unexpected to find that the glycol monobutyl ether component functions successfully in the ethoxylated alcohol surfactant-containing dye penetrant composition of the present invention as an effective extender at high dilution, that is with a high concentration of the glycol monobutyl ether, while at the same time not adversely affecting the sensitivity of the remaining dye penetrant composition in the cracks and flaws of the part.

The nonionic biodegradable solvents or carrier which can be employed as substantially the sole vehicle for the dye of the dye penetrant compositions according to the present invention are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above preferred class of nonionic biodegradable surfactant employed as carrier for the dye penetrant of the invention is a mixture of compounds which can be represented by the formula:

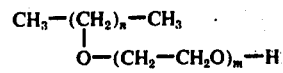

where $n$ is in the range from 9 to 13, and $m$ is an average of 3 to 12.

Although preferably each of the above-defined surfactants is formed of a mixture of two or more linear alkyl hydrophobic chains ranging from $C_{11}$ to $C_{15}$, as noted below, the surfactant can contain a single such chain formed from a single secondary aliphatic alcohol of the types described below.

The linear alkyl hydrophobic portion of the above defined surfactant is a mixture of $C_{11}$ and $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom in the alkyl hydrophobic chains to which the hydrophilic polyoxyethylene chain is attached will become a

group. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| Tergitol | 15-S-3 |
| | 15-S-5 |
| " | 15-S-7 |
| " | 15-S-9 |
| " | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant of the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as carrier or vehicle for the dye of the penetrant solution according to the invention, are prepared by reacting an alcohol or mixture of alcohols, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced possess random distribution of oxyethylene groups, as noted above.

Another process for preparing the above nonionic surfactants in the form of ethoxylates of linear secondary aliphatic alcohols, is described in U.S. Pat. No. 2,870,220.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9. Also, particularly effective dye penetrants are provided according to the invention employing a combination or mixture of the above Tergitols 15-S-5 and 15-S-9, and to which there can be added optionally Tergitol 15-S-3, as described in my above copending application Ser. No. 521,730.

The incorporation of the glycol monobutyl ether into the dye penetrant containing for example the above Tergitol 15-S-3, substantially improves the water washability of the resulting dye penetrant, employing such surfactant, which as noted above is essentially water insoluble.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The ethoxylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention preferably contains a fluorescent dye. Various types of fluorescent dyes can be employed including for example the dye marketed as Fluorol 7GA as well as other fluorescent dyes such as those marketed as Calcofluor Yellow, Azosol Brilliant Yellow 6GF; Rhodanine B, Rhodanine 6 GDN, Calcofluor White RW, Blancophor White AW, Auramine and Eosine G, and water soluble fluorescent dyes such as Blancophor FFG.

The dye penetrant composition employed according to the invention alternatively can contain non-fluorescent or daylight type dyes such as azo type dyes, e.g., xyleneazobeta-naphthol, Mefford No. 322 dye, believed to be o-tolueneazoxyleneazo-beta-naphthol, and the azo dyes marketed as Oil Red "O" and Sudan Red. These dyes conveniently can be employed where daylight or white light is only available, and particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the ethoxylated alcohol surfactant or carrier to produce the dye penetrant composition of the invention, can range from about 0.1 to 15, preferably about 0.5 to about 10, parts of the dye, or mixtures thereof, per 100 parts of the ethoxylated alcohol surfactant, by weight. In preparing the dye penetrant composition employed according to the invention, the dye is simply added to the ethoxylated alcohol carrier, in the desired proportion. The resulting dye penetrant composition has both high and low temperature stability.

The amount of the glycol monobutyl ether incorporated into the dye penetrant composition hereof containing ethoxylated alcohol surfactant and dye, generally ranges from about 10 to about 150%, preferably from about 20 to about 100%, by volume of the initial dye penetrant composition, that is, the sum of the ethoxylated alcohol surfactant and dye. If more than about 150% by volume of the glycol monobutyl ether component based on the sum of the thoxylated alcohol surfactant and dye is employed, the sensitivity of the dye penetrant composition commences to decay, probably due to the fact that at such high concentration of the glycol monobutyl ether component, the glycol ether solvent carries with it some of the dye remaining in the cracks and flaws of the part. The use of less than 10% by volume of the other components, of the glycol monobutyl ether substantially reduces the advantages of thinning which are sought to be obtained by incorporation of the glycol monobutyl ether component in the dye penetrant composition.

In carrying out the invention process, if necessary, the part or surface to be inspected first can be suitably prepared as for example by suitably cleaning and drying the part.

The liquid dye penetrant composition containing the glycol monobutyl ether is applied to the test specimen, for example by dipping same into a bath of the penetrant, or the penetrant can be poured or sprayed onto the surface of the test specimen. Preferably the dye penetrant composition hereof is sprayed on the specimen surface, such spraying being aided by use of the glycol monobutyl ether extender. The dye penetrant composition is maintained on the surface of the test body or specimen for a period sufficient to permit the composition to penetrate the cracks and imperfections in the part surface, e.g. for about 1 to about 5 minutes.

The above-noted water wash is then applied for preferentially removing the glycol monobutyl ether from the dye penetrant, the excess remaining dye penetrant composition, stripped of the glycol monobutyl ether, then immediately being removed or washed off the surface of the part being tested, as noted above, in the same wash operation, without being removed from the openings of the surface cracks or flaws. This washing operation can be accomplished by any suitable means such as by application of a plain water spray or a sprayed mixture of air and water, leaving a portion of the dye penetrant free of glycol monobutyl ether remaining in the cracks and defects of the part.

As previously noted, the glycol monobutyl ether has the ability of immediately abandoning the penetrant solution upon contact with water. This is due to the property of such glycol ether of having preferential affinity for water, and thus being preferentially removed first with the water wash, while momentarily leaving the dye penetrant containing dye and dye vehicle uniformly distributed over the surface of the part, and which is then finally removed by the water wash. Such immediate and momentary disassociation and removal of the glycol monobutyl ether from the basic penetrant formulation upon application of water, thus permits the remaining dye penetrant to have the same sensitivity and brightness properties as the initially formulated penetrant composition, prior to incorporation of such glycol ether, with the advantages that the removal of such nonvolatile solvent is accomplished rapidly by means of a water wash, followed immediately by removal of the remaining dye penetrant uniformly distributed over the surface of the part, in the same water wash, without the necessity of using a volatile type solvent for this purpose. When employing volatile type solvents for thinning dye penetrants, as in the prior art, it is necessary to wait for complete evaporation of the solvent and for the remaining penetrant to dry, before removal of remaining dye penetrant. If such volatile solvent-thinned penetrant is removed by the washing step before its solvent evaporates, the volatile solvent still present in the remaining penetrant in the cracks and flaws will affect the sensitivity of the dye penetrant.

Following washing and removal of glycol monobutyl ether and remaining dye penetrant composition from the part surface, followed by drying, the surface is then viewed under suitable lighting conditions, e.g. ultraviolet or black light when the dye in the dye penetrant is a fluorescent dye, to locate any cracks or defects on the surface of the body, as indicated by colored traces, for example, by fluorescent emissions, from the dye penetrant therein.

If desired, after removal of excess dye penetrant composition and drying the part surface, a developer composition can be applied to the part surface followed by removal of excess developer, as by means of an air blast. The part is then viewed under suitable lighting conditions, employing black light or fluorescent illumination when the dye penetrant contains a fluorescent dye. For this purpose, a dry powder or non-aqueous (volatile solvent base) developer composition can be employed. Preferred developer compositions for use in conjunction with the dye penetrant composition according to the invention, are those described in my U.S. Pat. No. 3,803,051, which is a dry powder developer containing fumed alumina, fumed silica, fumed titanium dioxide and talc, and in my U.S. Pat. No. 3,748,469, and which is a wet non-aqueous developer composition consisting essentially of isopropyl alcohol, talc and glycol monobutyl ether. The descriptions of such developer compositions contained in the above patents are incorporated herein by reference.

The following are examples of practice of the invention.

EXAMPLE 1

The following liquid dye penetrant was prepared and designated dye penetrant A:

| COMPONENTS | Parts by Weight |
|---|---|
| Tergitol 15-S-5 | 100 |
| Calcofluor White RW | 5 |
| Fluorol 7 G A | 1.5 |

To the above dye penetrant A was added glycol monobutyl ether in an amount of 10% by volume of composition A. The resulting dye penetrant composition containing glycol monobutyl ether is designated composition B.

The fluorescent dye penetrant composition B above was applied as by spraying, to one-half the surface of a chromium-plated brass test panel containing cracks 0.00002 to 0.0001 inch in width, closely distributed over its entire surface. A water wash was then applied by an air-water rinser over the coating of dye penetrant composition B on the test panel, causing preferential removal of the glycol monobutyl ether from the dye penetrant composition, and also instantaneously washing remaining dye penetrant, now free of glycol monobutyl ether, and corresponding to the initial dye penetrant A, from the surface of the test panel. The test panel was then dried. The dye penetrant washed from the surface of the panel was biodegradable.

The other half of the test panel surface was sprayed with dye penetrant A above, initially containing no glycol monobutyl ether. The excess dye penetrant was then removed by spraying a mixture of air and water over the panel surface. The test panel was then dried.

Both halves of the test panel surface were covered with a powder developer having the following composition, according to my above U.S. Pat. No. 3,083,051.

| COMPONENTS | Percent by Weight |
|---|---|
| Talc | 52 |
| Alumina | 35 |
| Silica | 4 |
| $TiO_2$ | 9 |

The above developer was permitted to dwell over the surface of the test panel for a period of about 2 minutes.

Excess developer composition was then carefully removed from the surface of the test panel by means of a gentle air blast.

Inspection of the two penetrant treated surfaces of the test panel under ultraviolet or fluorescent light, revealed fluorescent indications from numerous readily defined microcracks therein, the fluorescent indications on both sides of the test panel being in substantially equivalent concentration, with substantially the same brightness and sensitivity or optical intensity on both sides of the test panel.

From the above, it is seen that the glycol monobutyl ether, while serving as an extender and temporary carrier for the dye penetrant A, can be readily removed from the dye penetrant, so that the resulting dye penetrant has substantially the same fluorescent brightness and sensitivity characteristics as the dye penetrant A initially applied, in the absence of the glycol monobutyl ether extender. In addition, the dye penetrant solution washed from the first half of the test panel surface to which the composition B containing glycol monobutyl ether was applied, was biodegradable.

EXAMPLE 2

The procedure of Example 1 was repeated employing compositions corresponding to composition B of Example 1, but employing, respectively, proportions of glycol monobutyl ether to composition A, commencing with a proportion of 20% of glycol monobutyl ether to composition A, and in increments of 10% by volume up to a composition containing 150% of glycol monobutyl ether, by volume, to composition A.

Results in each case were obtained similar to the results of Example 1.

EXAMPLE 3

The procedure of Example 1 was repeated but employing the following dye penetrant composition, designated composition C:

| COMPONENTS | Parts by Weight |
|---|---|
| Tergitol 15-S-5 | 75 |
| Tergitol 15-S-9 | 25 |
| Calcofluor White RW | 2.5 |
| Fluorol 7 G A | 0.75 |

To the above dye penetrant composition C was added glycol monobutyl ether in an amount of 50% by volume of composition C. The resulting dye penetrant composition containing glycol monobutyl ether was designated composition D.

The dye penetrant composition D and dye penetrant composition C were applied to respective half sides or surfaces of an aluminum test panel having microcracks within the range of those noted for the test panel in Example 1.

In the case of the half panel surface coated with dye penetrant composition D, the air-water spray preferentially removed glycol monobutyl ether, followed almost instantaneously by removal of the remaining dye penetrant from the surface of the panel. The dye penetrant thus removed was biodegradable.

Following removal of remaining dye penetrant from each of the two half surfaces of the panel, and drying, both halves of the test panel surfaces to which penetrant composition D and penetrant C were applied, were covered with a powder developer of the type described in Example 1, following which excess developer composition was removed as described in Example 1.

Both halves of the test panel were then placed under fluorescent illumination and it was observed that both surfaces of the test panel disclosed fluorescent indications from the microcracks in the test panel, showing substantially the same concentration of numerous microcracks in both halves of the panel, with substantially corresponding brightness and definition in both half surfaces of the panel.

EXAMPLE 4

The procedure of Example 1 was substantially repeated except that a test panel was employed containing relatively gross cracks substantially greater than 0.0001 inch in width, and no developer composition was employed.

When the test panel was placed under fluorescent illumination, both half surfaces of the panel showed substantially the same concentration of fluorescent dye traces and of substantially the same brightness and resolution, detecting the location and size of the microcracks, and again indicating substantially the same sensitivity for dye penetrant composition B following removal of the glycol monobutyl ether, as in the case of dye penetrant A which initially contained no such glycol ether component.

EXAMPLE 5

The procedure of Example 1 was repeated except that dye penetrant A was replaced by a dye penetrant comprising 10 parts of Tergitol 15-B-5 and 1 part of daylight visible Oil Red "O" dye, by weight, the resulting dye penetrant composition designated E, and to such penetrant was added glycol monobutyl ether in amount about 60% by volume of composition E, the resulting composition designated F.

The compositions E and F were applied to half surfaces of an aluminum panel containing gross cracks and respective half surfaces of the test panel were processed as in the case of compositions A and B in Example 1.

Both half surfaces of the panel were then exposed to ordinary daylight, showing the same good clarity and definition, and substantially the same brightness, of the dye trace patterns for the cracks in both half surfaces of the panel.

From the foregoing, it is seen that the invention provides an effective biodegradable substantially non-flammable and non-toxic water washable dye penetrant composition thinned or extended by incorporation of glycol monobutyl ether, facilitating spraying of the composition on a test part and permitting rapid initial removal of the extender, with practically instantaneous removal of remaining dye penetrant in a single wash operation, the washed penetrant being biodegradable, followed by further processing of the dye penetrant coating as desired in the conventional manner for viewing under suitable, e.g. fluorescent, lighting conditions to obtain the same sensitivity and brilliance of dye traces as in the case of the same dye penetrant in the absence of glycol monobutyl ether, and avoiding the use of volatile extenders and thinners.

Since various changes and modifications of the invention will occur to and can be made readily by those skilled in the art without departing from the invention concept, the invention is not to be taken as limited except by the scope of the appended claims.

I claim:

1. A water washable biodegradable liquid dye penetrant composition for use in non-destructive testing for detecting cracks and flaws in the surface of an object, which consists essentially of (1) a single biodegradable nonionic surfactant which consists essentially of ethoxylates of linear secondary aliphatic alcohols, with the hydroxyl groups randomly distributed, the liner aliphatic portion of said alcohols being a mixture of alkyl chains containing in the range from 10 to 17 carbon atoms, and containing an average of from 3 to 12 moles of ethylene oxide, (2) a dye soluble in said surfactant and (3) glycol monobutyl ether as extender.

2. A dye penetrant composition as defined in claim 1, wherein said surfactant consists of ethoxylates of a mixture of alcohols having the formula:

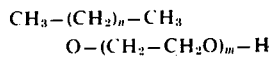

where $n$ is in the range from 9 to 13 and $m$ is an average of 3 to 12.

3. A dye penetrant composition as defined in claim 2, wherein said surfactant is selected from the group consisting of said ethoxylates of said mixture of alcohols, wherein $n$ ranges from 9 to 13, and $m$ is an averge of 3, 5, 7, 9, or 12.

4. A dye penetrant composition as defined in claim 1, wherein said dye is a fluorescent dye.

5. A dye penetrant composition as defined in claim 2, wherein said dye is a fluorescent dye and said dye is present in said composition in an amount ranging from about 0.1 to 15 parts, per 100 parts, by weight of said surfactant.

6. A dye penetrant composition as defined in claim 1, said glycol monobutyl ether being present in a proportion ranging from about 10 to about 150% of the sum of said surfactant and said dye, by volume.

7. A dye penetrant composition as defined in claim 4, said glycol monobutyl ether being present in a proportion ranging from about 10 to about 150% of the sum of said surfactant and said dye, by volume.

8. A dye penetrant composition as defined in claim 5, said glycol monobutyl ether being present in a proportion ranging from about 10 to about 150% of the sum of said surfactant and said dye, by volume.

9. A dye penetrant composition as defined in claim 2, said glycol monobutyl ether being present in a proportion ranging from about 20 to about 100% of the sum of said surfactant and said dye, by volume.

10. A dye penetrant composition as defined in claim 3, said glycol monobutyl ether being present in a proportion ranging from about 20 to about 100% of the sum of said surfactant and said dye, by volume.

11. A dye penetrant composition as defined in claim 5, said glycol monobutyl ether being present in a proportion ranging from about 20 to about 100% of the sum of said surfactant and said dye, by volume.

12. A dye penetrant composition as defined in claim 3, wherein $m$ in said surfactant is an average of 5.

13. A dye penetrant composition as defined in claim 12, wherein said dye is a fluorescent dye and said dye is present in said composition in an amount ranging from about 0.1 to 15 parts, per 100 parts, by weight of said surfactant, and said glycol monobutyl ether being present in a proportion ranging from about 10 to about 150% of the sum of said surfactant and said dye, by volume.

14. A dye penetrant composition as defined in claim 3, employing a combination of said biodegradable nonionic surfactants wherein $m$ is one of said surfactants is an average of 5 and $m$ in another of said surfactants is an average of 9.

15. A dye penetrant composition as defined in claim 14, wherein said dye is a fluorescent dye and said dye is present in said composition in an amount ranging from about 0.1 to 15 parts, per 100 parts, by weight of said surfactant, and said glycol monobutyl ether being present in a proportion ranging from about 10 to about 150% of the sum of said surfactant and said dye, by volume.

16. A dye penetrant composition as defined in claim 15, said glycol monobutyl ether being present in a proportion ranging from about 20 to about 100% of the sum of said surfactant and said dye, by volume.

* * * * *